United States Patent [19]

Kossove

[11] 4,363,320
[45] Dec. 14, 1982

[54] BREATHING AIRWAY

[76] Inventor: Michael Kossove, 1101 162nd St., Whitestone, N.Y. 11357

[21] Appl. No.: 187,970

[22] Filed: Sep. 17, 1980

[51] Int. Cl.³ ............................................. A61M 25/00
[52] U.S. Cl. .......................... 128/207.14; 128/200.26
[58] Field of Search ....................... 128/200.26, 202.28, 128/207.14, 207.15, DIG. 9, 10, 11, 207.17

[56] References Cited

U.S. PATENT DOCUMENTS

| | | | |
|---|---|---|---|
| 3,225,767 | 12/1965 | Smith | 128/200.26 |
| 3,538,913 | 11/1970 | Stolfi | 128/202.28 |
| 3,568,680 | 3/1971 | Raimo | 128/207.14 |
| 4,256,099 | 3/1981 | Dryden | 128/200.26 |

Primary Examiner—Henry J. Recla
Attorney, Agent, or Firm—James M. Deimen

[57] ABSTRACT

An improved breathing airway comprising at least two telescopingly engaged flexible elements enabling the airway to be adjusted to the proper length to fit the mouth and pharynx of a patient. To positively secure the adjusted length of the airway, a flap with protruberances extends from the outer element and is engageable with holes in the inner element. Thus, the outer and inner engaged elements can be positively secured at the correct measured mouth to pharynx length.

The untelescoped radius of curvature of each element differs from the other causing the radius of curvature of the airway to change as the elements are telescoped together. The radius of airway curvature is therefore automatically adjusted for curvature when the airway is set to desired length. Thus, one size airway of the present invention can substitute for several sizes of the prior art airways, the adjustment for the selected length automatically achieving the correct shape.

14 Claims, 6 Drawing Figures

BREATHING AIRWAY

BACKGROUND OF THE INVENTION

Breathing airways are well known medical devices used to insure an unobstructed passageway from the patient's upper pharyngeal region through his lips. In surgical situations and medical emergencies an unconcious patient's natural airway may become obstructed with the tongue. An airway generally consists of a curved portion to reach the pharynx while restraining the patient's tongue and a straight portion which passes through the lips and teeth. The straight portion must be rigid enough to resist involuntary biting which could close the airway passage through the teeth.

Airways can be constructed as enclosed conduits or open sections. An airway can be used to administer oxygen enriched gases and other therapeutic materials and can be used to guide a catheter into the respiratory tract as described in U.S. Pat. No. 3,756,244.

To accomplish the intended function, an airway must be of the correct size to fit the pharynx of the particular patient. The length and shape of the path between the lips and pharynx will vary considerably between an infant and a large adult. In the prior art, a correct fit between patient and airway is accomplished by having airways constructed to numerous sizes. This practice requires that medical users of airways such as operating rooms and ambulance services be supplied with multiple sizes of airways.

U.S. Pat. No. 3,538,913 discloses a telescoping collapsible airway to provide more convenient storage in a pocket or doctor's bag. This airway is of metal or hard plastic construction and provides no means for securing the telescoping body at intermediate positions before insertion in a patient.

SUMMARY OF THE INVENTION

The airway of the present invention reduces the need for medical users of airways to maintain supplies of airways of various sizes. The airway of the present invention comprises at least two telescoping elements which can be adjusted and secured at the desired length. The radius of airway curvature is automatically compensated when the airway is set to the selected length. Thus, one size of the present invention can substitute for several sizes of the prior art airways, the adjustment for the selected length automatically achieving the correct shape.

The medical officer, after measuring the approximate distance from lips to pharynx, merely telescopes the two elements together to the desired length and then snaps the securing means in place.

The advantage of a reduced inventory of airways is especially important for ambulance services which are restricted in the amount of medical equipment that can be carried. Reducing the number of airway sizes also reduces production and distribution costs.

These and other advantages of the invention will be evident to those skilled in the art from the following detailed description.

DESCRIPTION OF THE PREFERRED EMBODIMENT

Figure 1:
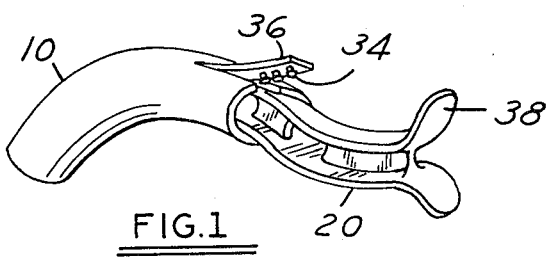
FIG. 1 is a perspective view of the adjustable airway.
Figure 2:
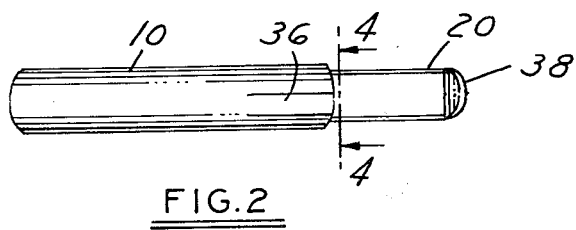
FIG. 2 is a top view of the adjustable airway.

Refering to FIG. 1, the airway device comrises two major elements, an outer conduit 10 and an inner member 20. Inner member 20 telescopes inside the hollow outer conduit 10. The length of the airway device can be thereby adjusted by slideably changing the relative positions of the two elements.

Figure 3A:
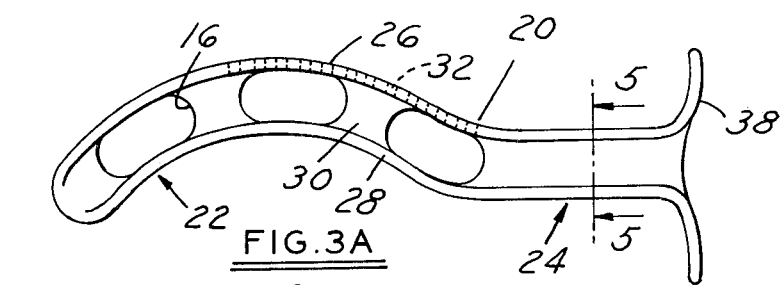
FIG. 3A is a side view of the inner member of the adjustable airway.
Figure 3B:
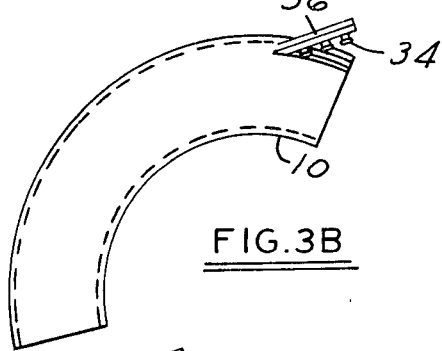
FIG. 3B is a side view of the outer member of the adjustable airway.
Figure 4:
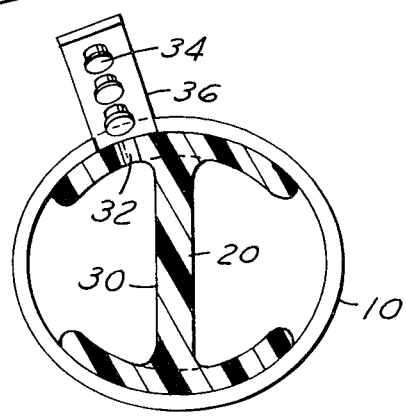
FIG. 4 is a transverse sectional view taken along the line 4—4 of FIG. 2; and,
FIG. 5 is a transverse sectional view of the inner member taken along line 5—5 of FIG. 3A.

The outer conduit 10 is substantially elliptical in cross-section as shown in FIG. 4 and is curved along its length as shown in FIG. 3B. Outer conduit 10 has at least one inwardly extending protuberance 34 near the upper end. Protuberance 34 may integrally extend from the wall of the outer conduit 10 or may extend from an integral flap 36 formed in the wall of the outer conduit 10 as shown in FIG. 3B. Preferably the protuberances 34 are formed with bulbous or enlarged ends as shown.

The size and shape of outer conduit 10 allow it to fit within the human mouth and pharynx. Outer conduit 10 and inner member 20 are constructed of a generally pliant or flexible material such as soft rubber or a flexible plastic commonly used for medical purposes.

Figure 5:
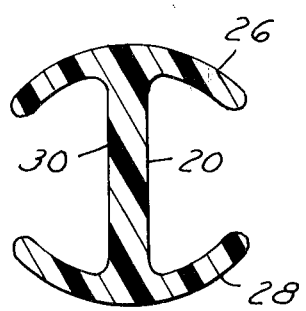

Inner member 20 has a substantially I cross-section as shown in FIG. 5 and is sized to slideably telescope inside outer conduit 10. The I section allows a catheter to be inserted and guided into the conduit 10 and further into the patient's pharynx. Referring to FIG. 3A, inner member 20 has a curved portion generally denoted by 22 and a relatively straight portion generally denoted by 24 integral therewith and extending therefrom. the cross-section of inner member 20 consists of an upper flange 26, a lower flange 28 and a connecting center web 30. Center web 30 has holes 16 in the curved portion denoted by 22 to reduce stiffness. In the straight portion denoted by 24 the center web 30 may be of increased thickness and the holes 16 are deleted to prevent collapse from biting forces.

Upper flange 26 is provided with a plurality of positioning holes 32 over a length at least sufficient to provide the difference between the maximum and minimum lengths of the airway. Positioning holes 32 are sized to accept the bulbous ends of protuberances 34 with an interference fit. The bulbous ends of the protuberances 34 provide a secure snap-in fit in holes 32 once the desired length is selected for the airway and member 20 and conduit 10 are telescoped together to the desired length. Thus, the airway cannot further telescope or elongate during insertion into the patient or removal from the patient.

As shown in the drawing figures, the holes 32 and the flap 36 with the protuberances 34 are asymmetrically located with respect to the central web 30 of the inner member 20. The asymmetric location permits the bulbous ends of the protuberances 34 to extend entirely through and beyond the holes 32 without interference with the central web 30.

Inner member 20 is provided with a retaining flange 38. Retaining flange 38 rests against the patient's lips or teeth and prevents the airway from extending too far into the pharynx. The curved portion 22 of inner member 20 has a somewhat smaller radius of curvature than outer conduit 10. The difference in radius of curvature results in an increasing binding friction between the two elements thereby aiding in the adjustment process and providing additional resistance to movement when in use. Thus, as the conduit 10 and inner member 20 are telescoped together to provide a decreasing overall length, the radius of curvature of the airway also decreases.

The above difference in radii allows the airway to better conform to the patient when properly adjusted. A patient with a short distance between pharynx and lips requires an airway with a smaller radius of curvature than a patient with a longer distance between pharynx and lips. The difference in radius and shape between the two elements allows the airway to automatically compensate for different patients as it is adjusted in length.

Numerous variations of the present invention are possible. For example, more than two securable telescoping elements can be employed. The cross-section of the inner member can be an elliptical conduit fitting within the outer conduit. The relative positions of the two elements can be reversed. For example, the I section can be at the pharynx end and the conduit at the lips end of the airway. Various restraining mechanisms, such as small transverse ribs engageable with complementary grooves can be substituted for the protuberances and holes disclosed above. Thus, modifications may be effected by those skilled in the art without deparating from the fair scope of the invention which is defined by the following claims.

I claim:

1. An improved breathing array for insertion into the mouth and pharynx comprising a substantially tubular and substantially arcuate first element, a second element having an arcuate portion telescopingly inserted into said first element for sliding engagement to provide a selectable length for said airway, said second element including means for providing fluid flow into said first element, the length of said first and second elements together being such that said airway is adjustable, when in use, to extend from the mouth of a patient and terminate in the region of the throat defined by the pharynx, the curvature of said arcuate elements being approximately that of the mouth and pharynx, and separate mutually engageable securing means on said first and second elements adapted to fixedly secure the first and second elements together at one of a plurality of selectable lengths.

2. The airway of claim 1 wherein said telescoping elements have differeing radii of curvature.

3. The airway of claim 1 wherein said securing means includes at least one protuberance on one element, and at least one hole in the other element, said protuberance engageable with said hole.

4. The airway of claims 1 or 3 wherein at least one of said elements includes a central web and said securing means are asymmetrically positioned relative to said central web.

5. The airway of claim 4 wherein said protuberances are located on a flap extending integrally from one element.

6. The airway of claims 1 or 3 wherein a portion of said securing means are located on a flap extending integrally from one element.

7. The airway of claim 1 wherein said second element includes a clamping portion adapted for engagement with a patient's jaws, said clamping portion including reinforcing means to resist the jaw clamping force.

8. An improved breathing airway for insertion into the mouth and pharynx comprising a flexible substantially tubular and substantially arcuate outer element and a flexible substantially arcuate inner element telescopingly inserted into said outer element, said second element including means for providing fluid flow into said first element, the length of said first and second elements together being such that said airway is adjustable, when in use, to extend from the mouth of a patient and terminate in the region of the throat defined by the pharynx, the curvature of said arcuate elements being approximately that of the mouth and pharynx, the radius of curvature of said inner element being less than the radius of curvature of said outer element thereby to cause the radius of curvature of the airway to decrease as the elements are telescoped together to decrease the length of the airway.

9. The airway of claim 8 including mutually engageable securing means on said outer and inner elements adapted to fixedly secure the outer and inner elements together at a selected length.

10. The airway of claim 9 wherein at least one of said elements includes a central web and said securing means are asymmetrically positioned relative to said central web.

11. The airway of claims 9 or 10 wherein said securing means includes at least one protuberance on one element, and at least one hole in the other element, said protuberance engageable with said hole.

12. The airway of claim 11 wherein said protuberances are located on a flap extending integrally from one element.

13. The airway of claims 9 or 10 wherein a portion of said securing means are located on a flap extending integrally from one element.

14. The airway of claim 8 wherein one of said elements includes a clamping portion adapted for engagement with a patient's jaws, said clamping portion including reinforcing means to resist the jaw clamping force.

* * * * *